United States Patent [19]

Bonne

[11] Patent Number: 4,507,558
[45] Date of Patent: Mar. 26, 1985

[54] SELECTIVE LEAK-DETECTOR FOR NATURAL GAS

[75] Inventor: Ulrich Bonne, Hopkins, Minn.

[73] Assignee: Honeywell Inc., Minneapolis, Minn.

[21] Appl. No.: 468,266

[22] Filed: Feb. 22, 1983

[51] Int. Cl.[3] .............................. G01F 1/74; G01J 5/58
[52] U.S. Cl. ..................................... 250/345; 250/343; 250/338
[58] Field of Search ............ 250/345, 344, 343, 338 R

[56] References Cited

U.S. PATENT DOCUMENTS

| | | | |
|---|---|---|---|
| 2,462,995 | 3/1949 | Ritzmann | 422/62 |
| 2,720,594 | 10/1955 | Hutchins | 250/346 |
| 2,741,703 | 4/1956 | Munday | 250/345 |
| 2,938,117 | 5/1960 | Schmidt | 250/255 |
| 3,851,176 | 11/1974 | Jeunehomme et al. | 250/343 |
| 4,288,062 | 9/1981 | Gupta et al. | 266/88 |
| 4,401,967 | 8/1983 | Miwa et al. | 338/34 |
| 4,447,397 | 5/1984 | Anouchi et al. | 422/94 |

FOREIGN PATENT DOCUMENTS 1431269 4/1976 United Kingdom ................ 250/343

OTHER PUBLICATIONS

E. E. Crisman and H. J. Gerritson, "A Methane Detector Based on Tuned Infrared Emitting Semiconductor Diodes", GRI Symposium on Current Research on Methane Detection and Measurement, Brown University, Chicago, Ill., (Aug. 17, 1979), pp. 177-198.

Primary Examiner—Bruce C. Anderson
Assistant Examiner—Constantine Hannaher
Attorney, Agent, or Firm—Omund R. Dahle

[57] ABSTRACT

An improved detector for combustible gases and which is able to discriminate between natural gas (methane and ethane) and other sources of methane (e.g. swamp gas, petrochemical and automotive) or other combustible gases by measuring the characteristic methane/ethane ratio of natural gas, based on infrared absorption of methane and ethane, in combination with another non-specific combustible gas detector.

7 Claims, 5 Drawing Figures

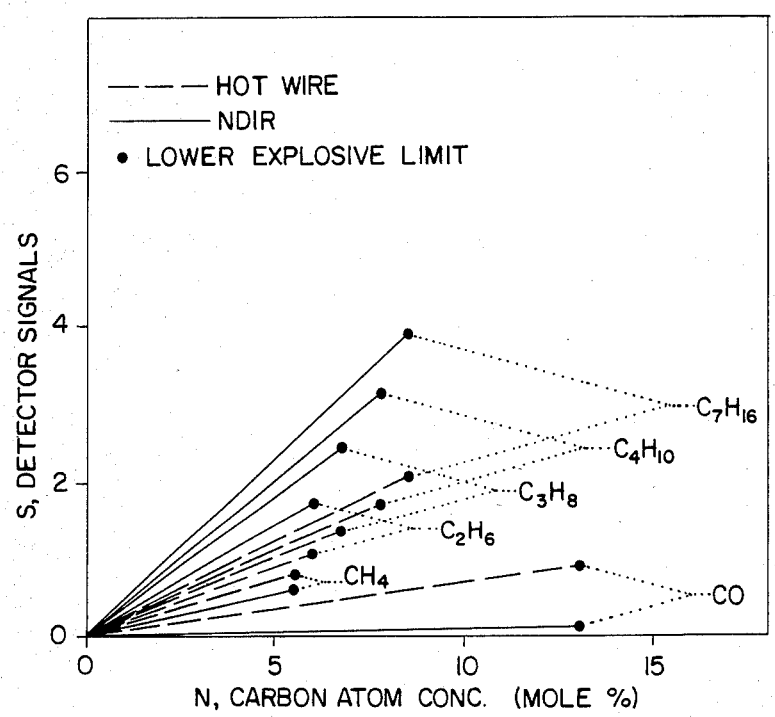
FIG. 4  QUALITATIVE RESPONSE OF HOT WIRE AND NDIR DETECTORS TO VARIOUS GASES.
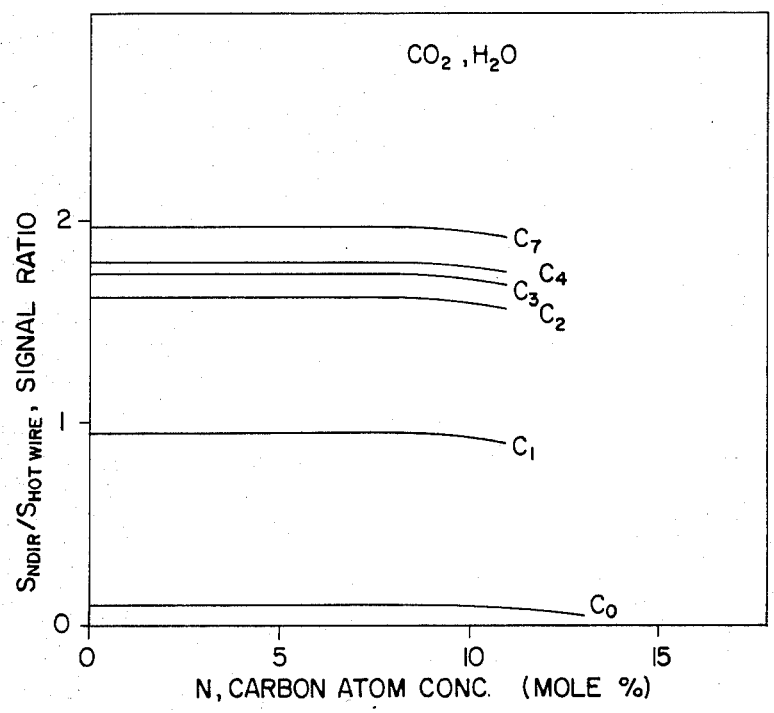
FIG. 5  RATIO OF NDIR TO HOT WIRE DETECTOR SIGNALS FOR VARIOUS GASES.

ns need reliable, sensitive, rugged and economic detectors that are specific to natural gas. Conventional gas-leak detectors are either non-selective and thus respond to any combustible gas or else they are specific to hydrocarbon gases.
SELECTIVE LEAK-DETECTOR FOR NATURAL GAS

BACKGROUND AND SUMMARY OF THE INVENTION

The present invention relates to an improved detector for natural gas, and which is able to discriminate between natural gas (methane and ethane) and other sources of methane or other combustible gases, and is based on infrared light absorption of methane and ethane in combination with a non-specific combustible detector.

Natural gas service, distribution and pipeline companies need reliable, sensitive, rugged and economic detectors that are specific to natural gas. Conventional gas-leak detectors are either non-selective and thus respond to any combustible gas or else they are specific to hydrocarbon gases.

The present invention is designed to discriminate between low concentrations of natural gas (i.e. pipeline leaks) and other methane sources (i.e. swamp gas, petrochemical or automotive) by measuring the characteristic methane/ethane ratio of natural gas, as well as by utilizing a combustible gas sensor. This invention is based on infrared light absorption of methane and ethane in combination with another non-specific combustible gas detector whereby the apparatus has the ability to detect, non-specifically, the presence of a combustible gas, and to define the nature of the combustible gas.

BRIEF DESCRIPTION OF THE DRAWINGS

FIGS. 4 and 5 are graphical presentations of the response of the NDIR and hot wire detectors to various gases.

DESCRIPTION

Figure 1:
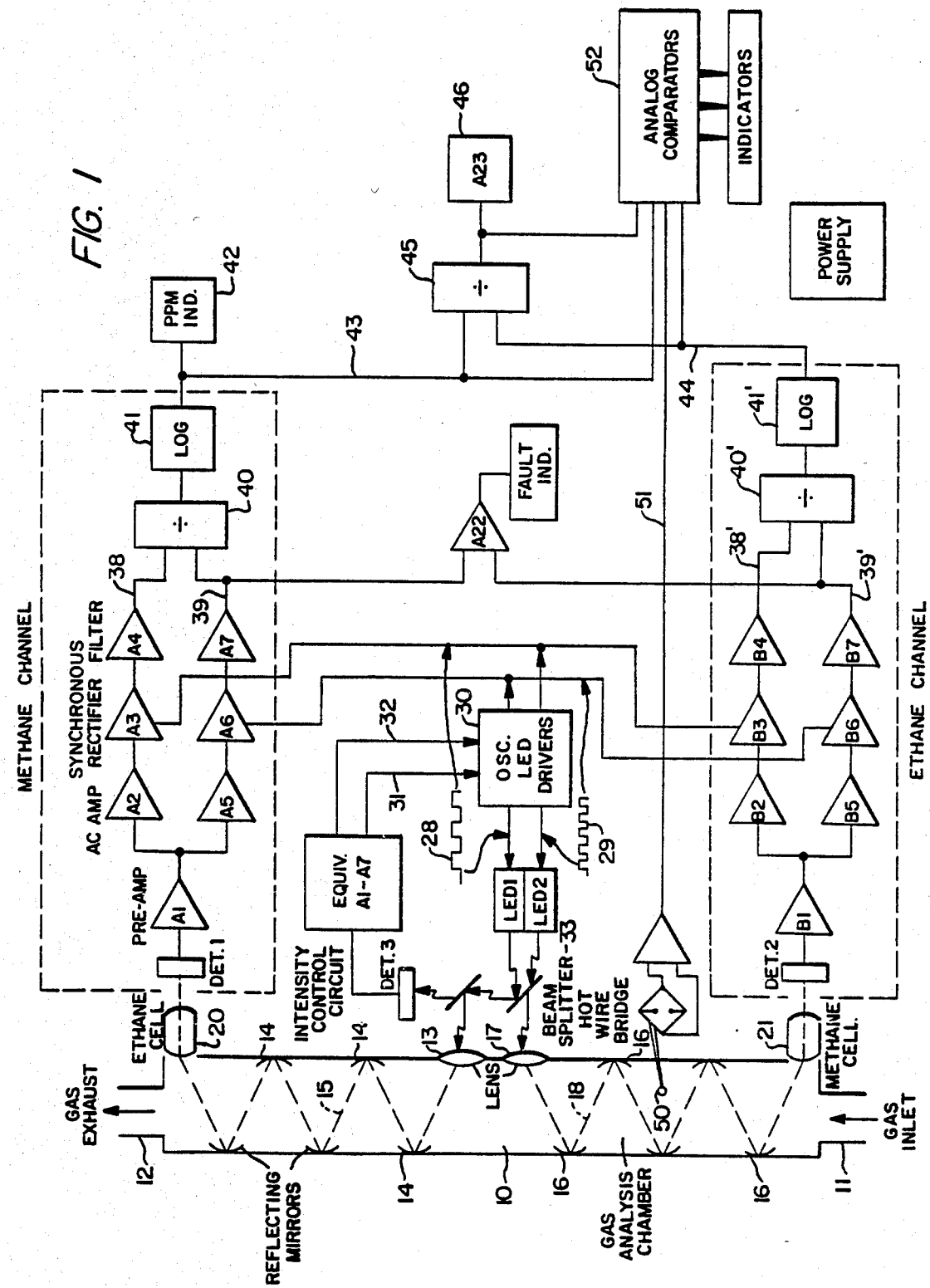
FIG. 1 is a block diagram of the gas sensor and associated analog electronic circuits.

The natural gas detector of FIG. 1 utilizes two types of detection methods including both NDIR (non-dispersive infrared) detectors and non-specific combustible detectors such as a hot-wire catalytic combustible detector, a thick film ZnO or SnO type non-specific combustible detector or other non-specific type hydrocarbon detector. The initial portion of the description will center on the two NDIR channels which detect and measure the concentrations of methane and ethane separately. The signals from these two NDIR signals are then compared. Natural gas is a mixture of methane and ethane and consists mostly of methane with smaller amounts of ethane (1-5%), therefore to determine whether the measured methane signal is from a natural gas leak, the concentration of ethane can be measured and compared with the methane concentration. If the ratio of the concentrations corresponds to the ratio expected in natural gas, then leaking natural gas is assumed to be the cause. If the ratio is outside of an acceptable ratio for natural gas (as would happen if swamp gas were the source) then natural gas is not indicated.

Referring now more specifically to FIG. 1 there is shown a gas analysis chamber 10 having a gas inlet 11 and a gas outlet 12. Two sources of electronically modulated infrared light, that is, two light emitting diodes, LED1 and LED2, emit IR through lens 13 into the gas analysis chamber 10. The light beam 15 is reflected a number of times within the chamber by reflecting mirrors 14 before exiting the chamber to impinge on IR detector DET1. Similarly the two diodes emit IR through lens 17 into the chamber 10 and the IR light beam 18 is reflected within the chamber by mirrors 16 and exits to impinge on IR detector DET2.

Figure 2:
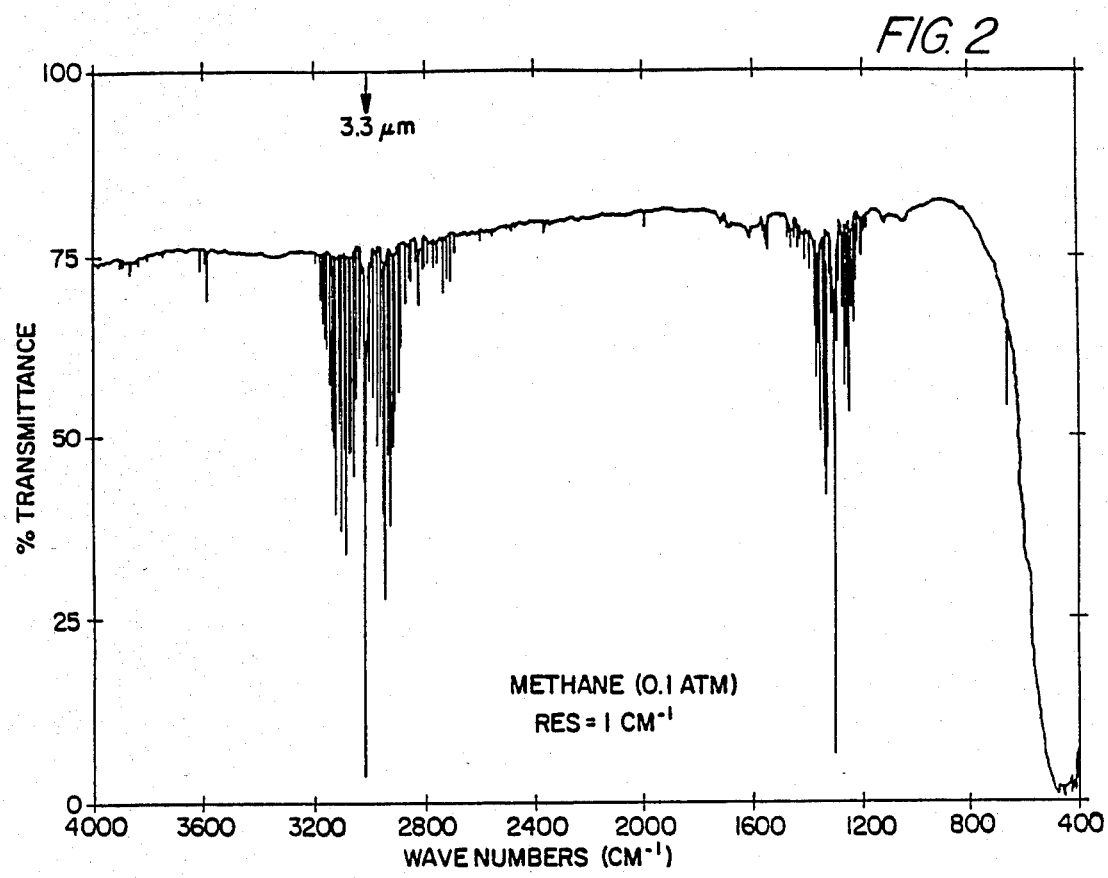
FIG. 2 is a graphical representation of the infrared transmission spectrum of methane at 0.1 atm taken with a Fourier Transform Spectrometer (Instrument resolution32 1 cm$^{-1}$).
Figure 3:
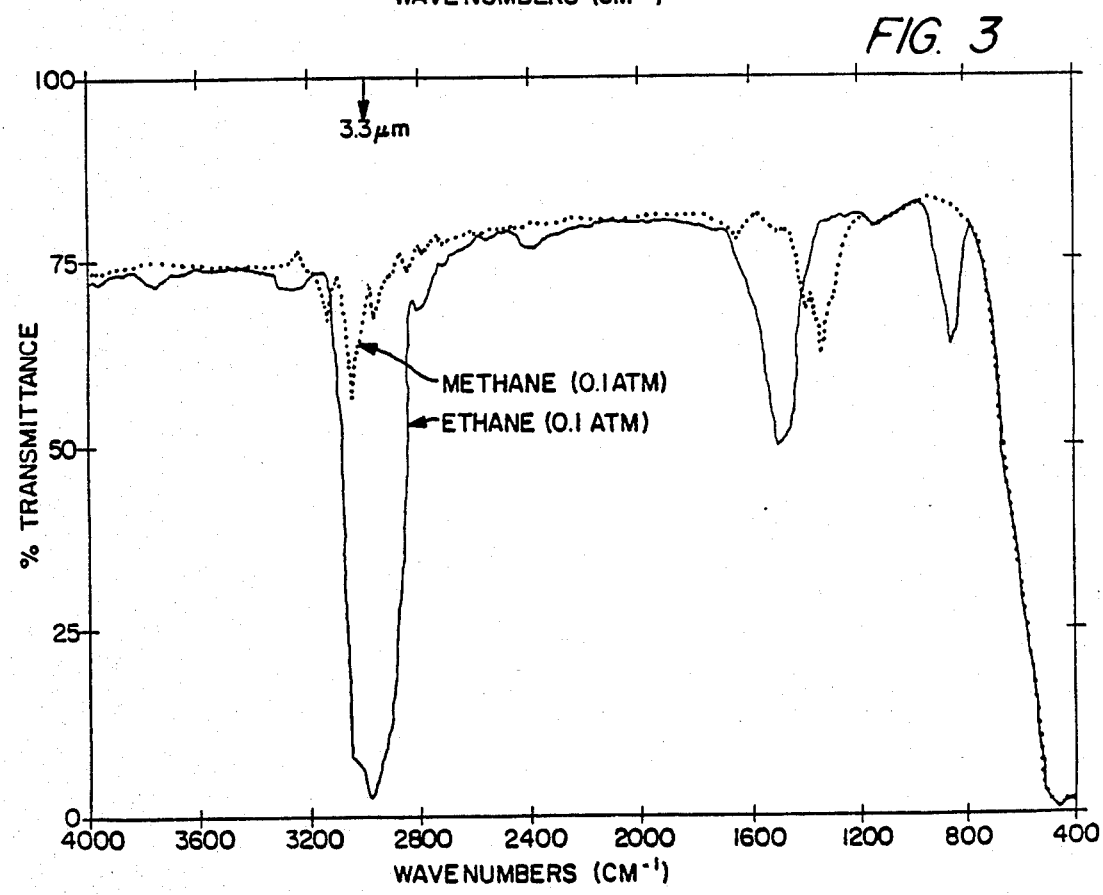
FIG. 3 is a graphical representation of the infrared transmission spectrum of methane and ethane (Instrument resolution = 32 cm$^{-1}$).

As shown in FIG. 2, the infrared transmission spectra of methane is composed of relatively narrow absorption lines within a group of lines or band. If light from an LED with a center wavelength of about 3.3 microns (3000 cm$^{-1}$) is sent through a gas sample containing methane, then the detected output power is reduced dependent on the concentration of the methane. However, the absorption spectra of methane and ethane overlap (FIG. 3). Part of the arrangement of this invention is the apparatus for determining the concentrations of both methane or ethane irrespective of the concentration of the other gas. This is accomplished by the gas absorption cells placed in front of the detectors as shown in FIG. 1.

The absorption of the LED light by either methane or ethane occurs only in very narrow bands. Therefore, most of the LED spectrum will pass unattenuated through a cell filled with either methane or ethane. Because the individual absorption lines of methane do not in general occur at the same wavelengths as those of ethane, different parts of the LED spectrum will be absorbed by the two gases. Therefore, if the light from the LED is passed through an optical test cell 10 which contains a certain concentration of methane and ethane, then absorption will occur in the optical spectrum at wavelengths corresponding to both methane and ethane and the concentrations of the gases cannot be determined because each gas has an effect on the detected output.

In this natural gas detector, the LED light is split into two paths 15 and 18, each of which travels through the same test cell 10. Before optical detection, however, one beam 15 passes through a gas cell 20 filled with ethane. The other beam 18 passes through a cell 21 filled with methane. In passing through the methane cell 21, all of the light at the absorption lines of methane are removed. Therefore, the concentration of methane in the gas test cell 10 has practically no effect on the detected output. Only the ethane in the test cell would affect the detected power in that beam. The concentrations of ethane in the test cell can be determined without an error caused by methane in the test cell, and thus the channel to be described including DET2 is labeled the ethane channel and determines the ethane concentration. Likewise in passing through the ethane cell 20, practically all of the light 15 at the absorption lines of ethane are removed. Therefore, the concentration of ethane in the gas test cell 10 has no effect on the detected output. Only the methane in the test cell affects the detected power in that beam. The concentration of methane in the test cell can be determined without an error caused by ethane in the test cell, and thus the electronic channel to be described below including detector DET1 is labeled the methane channel and determines the methane concentration.

The description continuing below refers more closely to the electronic portion of the system of FIG. 1. This embodiment shows and describes an electronic analog system but it is understood that the invention can be implemented equally as readily with a digital-microprocessor based approach. The analog system of FIG. 1 requires that the two LEDs, i.e. LED1 and LED2, be driven at a different repetition rate by two square wave generators in block 30 (Osc. LED Drivers). Two different repetition rate square waves are shown schematically at 28 and 29.

LED1 emits a spectrum of light centered around 3.32 microns and LED2 serves as a reference diode which emits at a wavelength outside of the 3.32 micron band. To correct for variations in the output of the LEDs due to temperature changes, a detector DET3 monitors the intensity of the LED light sources. Negative feedback loops connected back to the drivers at 31 and 32 sense variations in the light outputs of each LED by means of synchronous rectification, and independently adjusts the output current of the signal generators to keep the intensity constant. The output of the two adjacent LEDs is divided by common beam splitter means 33 which directs part of the light to detector DET3 and the intensity control circuit, part of the light into the cell or chamber 10 through lens 13 to become beam 15 and part through lens 17 to become beam 18. The optical path 15 through the upper half of the cell gives a measure of methane in ppm (parts per million). The lower half of the light path 18 providing the means of sensing ethane, uses identical circuitry to that of the upper path. Therefore, a description of the methane channel components will serve for both as well as for the intensity control circuit.

Because the LEDs are driven at different repetition rates, the contribution of each diode to the detector voltage can be determined by the outputs of two tuned phase locked amplifiers synchronized to the individual pulsed rates. By comparing the ratio of the two outputs when a gas was present to the value for an empty cell, the amount of absorption of the light from LED1 due to methane is determined. The amount of absorption is exponentially related to the gas concentration. Therefore, methane in parts per million (ppm) is accurately determined by taking the log of the absorption.

As shown in FIG. 3, the absorption of ethane occurs very near 3.32 microns (3000 wave numbers). Therefore, an LED emitting at 3.32 microns can be used to detect both gases methane and ethane. The described system uses two LEDs, one emitting at 3.32 microns and one at 3.8 microns. For natural gas detection, the output of each LED is split into two parts. The optical path through the upper half of the test cell gives a measure of methane in ppm. The ethane absorption cell is placed in front of detector DET1 to eliminate the portion of the optical signal which would be affected by the presence of ethane in the gas.

The lower light path passes through a methane cell (which eliminates any light at the methane absorption lines) and onto detector DET2 of the ethane channel. Therefore, the light at detector DET2 is not sensitive to the concentration of methane in the test cell. It is, however, sensitive to absorption due to ethane and longer carbon chains present in natural gas. The ratio of the light reaching detector DET2 from LED1 and LED2 is determined and an estimate of ethane concentration is obtained. This estimate is then compared to the estimate of methane concentration. If the comparison shows a gas mixture of methane to ethane of between 100:1 and 20:1, an indicator such as a light is turned on indicating the presence of natural gas or the relative amount of "ethane". This also permits the discrimination between natural gas and propane.

The upper light path 15 passes through the ethane absorption cell 20 and into the methane channel at detector DET1. The detector feeds a pre-amp A1. The detector pre-amp A1 is a current-to-voltage converter using a high quality op amp such as a OP07E op amp to minimize the effects of low source impedance, offset voltage and temperature drift. Since the IR light into detector DET1 has a component from LED1 and a component from LED2, there are two signals at the output of pre-amp A1. Two parallel signal channels are used at this point. One channel includes amp A2, synchronous rectifier A3 and filter A4 while the other channel includes the similar components A5, A6 and A7. One of these synchronous rectifiers A3 is driven at the same frequency as LED1 and the other A6 is driven at the same frequency as LED2. Filters A4 and A7 using OP07E op amps convert the outputs of the synchronous rectifiers to DC levels, one proportional to the intensity of the light received from LED1 and the other proportional to the light intensity of the reference diode, LED2. Output lines 38 and 39 from filters A4 and A7 are connected to the two inputs of a divider 40.

The ratio of the light intensity of the methane signal to the reference signal is thus determined by Analog Devices AD534K multiplier-divider 40 connected for division. An advantage of taking a ratio of the intensities is that it reduces the effect of front end sensitivity changes due to temperature variations or scatting due to dust. The ratio signal then passes to an Intersil 8048 log amplifier 41 to convert the ratio of optical intensities to methane concentration. The read out appears on a meter 42 calibrated in ppm (parts per million).

The lower ethane channel which provides the means for diagnosing the presence of ethane uses identical circuitry to that of the upper channel, and the comparable preamp, ac amp's, synch rectifiers and filters are identified as B1 through B7. The output of the filters B4 and B7 is connected to divider 40', the ratio signal from the divider then passing to log amplifier 40'.

To discriminate between swamp gas (methane) and natural gas, the ratio of the outputs 43 and 44 of the methane and ethane log amplifiers is determined by a third divider 45 and fed to a comparator 46, such as type CMP-01. If the ratio of methane to ethane is between 100:1 and 20:1 a light is turned on indicating natural gas. This type comparator function may be accomplished by feeding the output into two CMP-01 comparators used as a window detector.

Previously set out was the combination of a non-specific combustible detector with the two NDIR detectors so that discrimination against gasoline vapors, CO, and other combustibles can be provided. Such a detector, such as a hot wire catalytic combustible detector 50 located in chamber 10 and connected in a conventional bridge circuit provides an electrical output which is amplified and fed on conductor path 51 to one input of analog comparator means 52. The comparator means 52 also receives an input from conductor 43, from conductor 44 and from the output of divider 45.

This combination detector is based on the synergism between the NDIR approach using the absorption due to the vibrational—rotational exitation of the carbon—hydrogen bond at 3.3 micrometers and the hot wire catalytic (or other non-specific, total combustibles) approach.

The unknowns are generally a concentration of a gas like CO, $H_2$, $CH_4$, $C_2H_6$, $C_7H_{16}$, $CO_2$, $H_2O$, $O_2$ or $N_2$; measured values are absorption channels at three IR wavelengths, two near 3.3 microns, one IR wavelength near 3.4 (away from CH absorption) and the temperature of a hot wire combustible analyzer. These two detection methods, that is NDIR and hot wire, provide responses that are not only different for different combustible gases, but are also different from each other.

Referring to FIG. 4 there is shown graphically a qualitative response of hot wire and NDIR detectors to various gases. This figure as well as the next are estimated curves projected from a limited amount of experimental data. FIG. 5 shows graphically the ratio of NDIR to hot wire detector signals for various gases. In other words, the ratio of detector signals $S_{NDIR}/S_{HOT-WIRE}$) is different for different gases, as shown qualitatively in FIG. 5. It is the value of this ratio or an equivalent characteristic that makes it possible to identify the nature of the sample gas in the detectors. A few examples illustrate this:

The presence of $N_2$ or $O_2$ will give a "zero" signal from both detectors.

CO and $H_2$ will give hot wire signals but essentially a zero NDIR signal at 3.3 microns, i.e. the above ratio will be zero.

For hydrocarbons of increasing molecular weight, the ratio of NDIR signals to hot wire increases.

$H_2O$ and $CO_2$ may give a weak NDIR signal but no hot wire signal. The result may be a very large ratio.

Discrimination between CO, $CH_4$ (swamp gas), natural gas and gasoline vapors in residential areas is provided as follows: Assuming that it is unlikely to find large concentrations of ethane, large signals from all the three channels (hot wire and two NDIR) indicates gasoline unless the ratio of the two NDIR channels indicates methane or natural gas; large hot wire and negligible NDIR signals indicate CO and/or $H_2$.

The embodiment of the invention in which an exclusive property or right is claimed are defined as follows:

1. A selective detector apparatus of natural gas and of other combustible gases which is designed to distinguish between natural gas on the one hand, which is composed principally of a mixture of methane and ethane having a ratio between 100:1 and 20:1, and on the other hand other combustible gases such as methane, ethane, CO, $H_2$, gasoline vapors, propane or others, the apparatus comprising:
    an NDIR detector channel sensitive to methane gas and providing a first output signal which varies as a function of the concentration of methane gas;
    an NDIR detector channel sensitive to ethane gas and providing a second output signal which varies as a function of the concentration of ethane gas;
    a non-specific combustible detector sensitive to combustible gases and providing a third output signal when combustible gases are present;
    a gas analysis chamber having a gas inlet and a gas outlet and including said NDIR detectors and said non-specific combustible detector;
    first ratio determining means receiving said first and second signals and providing a ratio output signal indicating the ratio of methane to ethane;
    first comparator means indicating the presence of natural gas when said first ratio falls in the range between 100:1 and 20:1;
    and further comparator means receiving said first and third output signals and said ratio signal to provide an indicator of and identity of other combustible gases or $H_2$ or CO.

2. The apparatus according to claim 1 and further comprising:
    second ratio determining means in said further comparator means receiving said NDIR detector signals and said third output signal and providing a ratio output signal indicating the ratio of the NDIR signals to the third signal from the non-specific combustible detector.

3. The apparatus according to claim 1 in which the two NDIR channels each include a log amplifier because the amount of absorption is exponentially related to the gas concentration whereby concentration is accurately determined in taking the log of the absorption to provide said first and second output signals.

4. The apparatus according to claim 1 in which said non-specific combustible detector is a hot-wire catalytic detector.

5. The apparatus according to claim 4 in which said hot-wire catalytic detector is connected in a bridge circuit to provide an output which is a function of the carbon atom concentration in mole percent.

6. The apparatus according to claim 1 in which said non-specific combustible detector is a thick film ZnO type detector.

7. The apparatus according to claim 1 in which said non-specific combustible detector is a thick film SnO type detector.

* * * * *